United States Patent [19]

Imada et al.

[11] Patent Number: 4,514,420
[45] Date of Patent: Apr. 30, 1985

[54] ANTIFIBROTIC AGENT

[75] Inventors: Isuke Imada, Izumi; Masazumi Watanabe, Kawanishi, both of Japan

[73] Assignee: Takeda Chemical Industries, Ltd., Osaka, Japan

[21] Appl. No.: 479,074

[22] Filed: Mar. 25, 1983

[30] Foreign Application Priority Data

Apr. 6, 1982 [JP] Japan .................. 57-57474

[51] Int. Cl.³ .................. A61K 31/12; A61K 31/19; A61K 31/215
[52] U.S. Cl. .................. 514/689; 514/532; 514/557
[58] Field of Search .................. 424/331, 317, 385

[56] References Cited

U.S. PATENT DOCUMENTS 4,139,545  2/1979  Morimoto .................. 424/308
4,248,892  2/1981  Kanamaru .................. 424/317
4,271,083  6/1981  Morimoto et al. .................. 260/396 R
4,358,461 11/1982  Maki et al. .................. 424/331

OTHER PUBLICATIONS

J. Uitto et al., Clin. Chem. Acta 30:741–744, 1970.

Primary Examiner—Albert T. Meyers
Assistant Examiner—John W. Rollins, Jr.
Attorney, Agent, or Firm—Wenderoth, Lind & Ponack

[57] ABSTRACT

Compounds of the formula

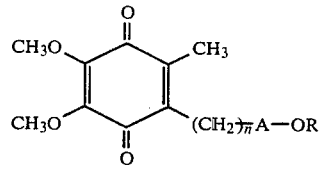

wherein A is methylene or carbonyl, n is an integer of 2 to 21, inclusive, and R is hydrogen or lower alkyl, are effective for the prophylaxis or treatment of mammals suffering from fibrosis due to excessive collagen accumulation.

10 Claims, No Drawings

ANTIFIBROTIC AGENT

The present invention relates to an agent for the prophylaxis or treatment of mammals suffering from fibroses.

In view of the excessive deposits of collagen in the tissues of man and animals with such diseases as hepatic and pulmonary fibroses, inhibitors of collagen biosynthesis have been investigated and evaluated for possible use as drugs for the prophylaxis and treatment of such diseases. However, the inhibitors of collagen biosynthesis found so far have the disadvantage that because of the toxicity inherent therein, such as the toxicity acknowledged to be possessed by $\beta$-aminopropionitrile, as an example, they cannot be repeatedly administered.

The research we conducted to develop a collagen biosynthesis-inhibiting compound that would lend itself well to repeated administration resulted in the finding that a compound of the following general formula (I) has such a collagen biosynthesis-inhibiting activity and a low toxicity.

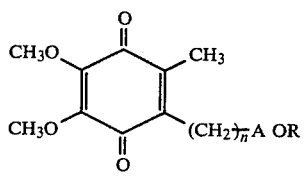

(A is a methylene group or a carbonyl group; n is an integer of 2 to 21, inclusive; R is a hydrogen atom or a lower alkyl group).

More particularly, this invention relates to a method for prophylaxis or treatment of a mammal suffering from fibrosis due to excessive collagen accumulation, which comprises administering to the mammal an effective amount of a compound of the formula (I); or a pharmaceutical composition for such prophylaxis or treatment which contains an effective amount of a compound of the formula (I) and a pharmaceutically acceptable carrier, vehicle or diluent therefor.

Referring to the above general formula (I), the lower alkyl group R is a group of 1 to 3 carbon atoms such as methyl, ethyl, etc., n is preferably an integer of from 7 to 11, inclusive, and A is preferably a methylene group. When A is a methylene group, the terminal hydroxyl group shown by OR may be protected by a protective group such as an acetyl group. As examples of the compound (I) wherein A is a methylene group and OR is a protected hydroxyl group, there are mentioned 6-(10-acetoxydecyl)-2,3-dimethoxy-5-methyl-1,4-benzoquinone, 6-(9-acetoxynonyl)-2,3-dimethoxy-5-methyl-1,4-benzoquinone, etc.

A particular group of compounds are those of general formula (I) where A is a methylene group and n is 9.

The compound of general formula (I) has protocollagen proline hydroxylase-inhibiting activity and collagen biosynthesis-inhibiting activity as described below.

(1) Protocollagen proline hydroxylase-inhibiting activity

This inhibitory activity was assayed by the procedure of R. E. Rhoads et al. (Methods in Enzymology XVII B, 306 (1971)) using a partially purified enzyme preparation derived from chick embryos in accordance with the methods of K. I. Kivirriko et al. and J. Halme et al. (J. Biol. Chem. 242, 4007 (1967) and Biochem. Biophys. Acta 198, 460 (1967), and, as a substrate, (Pro-Pro-Gly)$_5$·4H$_2$O (Protein Research Foundation, Osaka). In this assay, the partially purified enzyme preparation was used in the amount of 100 $\mu$g as protein. The results are shown in Table 1.

TABLE 1

| Compound (I) | Concentration ($\mu$M) | % Inhibition |
|---|---|---|
| A:CH$_2$ n:3 R:H | 25 | 68 |
| A:CH$_2$ n:9 R:H | 20 | 37 |
| A:CO n:3 R:CH$_3$ | 50 | 47 |
| A:CO n:3 R:H | 20 | 57 |
| A:CO n:7 R:H | 20 | 35 |
| A:CO n:9 R:H | 20 | 31 |
| A:CO n:9 R:CH$_3$ | 20 | 21 |

(2) Collagen biosynthesis inhibiting activity

Basically in accordance with the method of R. A. Salvador et al. [Arch. Biochem. Biophys. 174, 382 (1976)], 0.2 mg/kg of each test compound was intraperitoneally administered to rats of SD strain (♀, 3 weeks old) once daily for 6 consecutive days and the collagen content of the uterus was compared with the control value. The results are shown in Table 2.

TABLE 2

| | Test compound | Body weight of rats* (g) | Collagen content of uterus | Degree of inhibition** |
|---|---|---|---|---|
| (A) | Control | 73 ± 6 | 1.64 ± 0.3 | — |
| (B) | 17$\beta$-Estradiol | 73 ± 3 | 3.45 ± 0.11 | — |
| (C) | 17$\beta$-Estradiol + compound of formula (I) (n:9, A:CH$_2$, R:H) | 69 ± 6 | 2.94 ± 0.28 | 28 |

(Note)
*Rats were used in groups of 3. Initial body weights = 41 ± 2 ~ 42 ± 4 g.

**Degree of inhibition (%) = $\frac{(B) - (C)}{(B) - (A)} \times 100$

The compound (I) is very low in toxicity. By way of example, the administration of compound (I) [n:9, A:CH$_2$, R:H)] by gastric gavage to rats in a 5-week regimen of 2500 mg/kg/day caused no abnormalities in body weight, food intake, urinalysis and blood tests.

The compound (I) of this invention can be used as an antifibrotic drug for the prophylaxis and treatment of organ fibrosis in animals and especially in mammalian animals (e.g. laboratory animals such as rabbit, rat, mouse, etc., pet animals such as dog, cat, etc., and human being). Fibrosis is a general disease name denoting all the diseases occurring from an excessive accumulation of collagen in tissues, and covering, but not being limited to, such diseases as pulmonary fibrosis, hepatocirrhosis, nephrosclerosis, arteriosclerosis, scleroderma, myelofibrosis, chronic arthritis, rheumatoid arthritis, etc.

For use as a prophylactic or curative drug for fibrosis, the compound (I) of this invention can be orally or otherwise administered, either as it is or as formulated with appropriate physiologically acceptable carriers, excipients or diluents, in such dosage forms as powders, granules, tablets, capsules, injections, etc. The dosage depends on such factors as kind of disease, symptoms, subject, route of administration, or dosage forms, but in case of parenteral administration such as injection, the daily dose as the compound (I) is about 25 mg to 500 mg (0.5 mg to 10 mg/kg), preferably 50 mg to 250 mg (1.0 mg to 5 mg/kg) for an adult human, and in case of oral administration, the daily dose is about 500 mg to 5000 mg (10 mg to 100 mg/kg), preferably 1000 mg to 2500 mg (20 mg to 50 mg/kg) for an adult human.

The composition of this invention contains a drug of dosage unit form. This means a drug containing a daily dose of the compound [I] to be described above, or its multiples (up to 4 times), or its measures (down to 1/40), which is in a physically separate unit form suitable for administering as a medicine. Each dosage unit generally contains 0.3 mg to 250 mg of the compound [I]. Among them, an injection ampoule preferably contains 0.3 mg to 30 mg, and each of the other forms preferably contains 10 mg to 250 mg of the compound [I].

The compounds of general formula (I) wherein n is an integer of 2 to 9 have been described in U.S. Pat. No. 4,139,545 and the compounds (I) wherein n is an integer of 10 to 21 have been described in European Patent Publication No. 21841.

EXAMPLE 1

| Capsules | |
|---|---|
| Compound (I) (n:9, A:CH$_2$, R:H), namely, 2,3-dimethoxy-5-methyl-6-(10'-hydroxydecyl)-1,4-benzoquinone | 30 mg |
| Microcrystalline cellulose | 30 mg |
| Lactose | 57 mg |
| Magnesium stearate | 3 mg |
| Total | 120 mg |

The above components were mixed and filled into gelatin capsules by the accepted pharmaceutical procedure to provide an encapsulated drug preparation.

EXAMPLE 2

| Tablets | |
|---|---|
| Compound (I) (n:9, A:CH$_2$, R:H) | 30 mg |
| Lactose | 44 mg |
| Starch | 10.6 mg |
| Starch (for size) | 5 mg |
| Magnesium stearate | 0.4 mg |
| Carboxycellulose calcium | 20 mg |
| Total | 110 mg |

The above components were mixed and processed into tablets.

EXAMPLE 3

| Soft capsules | |
|---|---|
| Compound (I) (n:9, A:CH$_2$, R:H) | 30 mg |
| Corn oil | 110 mg |
| Total | 140 mg |

The above components were mixed and the solution was processed into soft capsules by the established pharmaceutical procedure.

What is claimed is:

1. A method for treatment of a mammal suffering from fibrosis due to excessive collagen accumulation, which comprises administering to the mammal an effective amount of a compound of the formula:

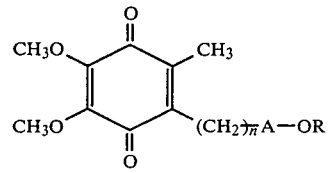

wherein A is methylene or carbonyl, n is an integer of 2 to 21, inclusive, and R is hydrogen or lower alkyl.

2. A method as claimed in claim 1, wherein n is an integer of 7 to 11, inclusive.

3. A method as claimed in claim 1, wherein A is a methylene group.

4. A method as claimed in claim 1, wherein A is a methylene group and n is 9.

5. A method as claimed in claim 1, wherein the compound is 2,3-dimethoxy-5-methyl-6-(10'-hydroxydecyl)-1,4-benzoquinone.

6. A method as claimed in claim 1, wherein the fibrosis is pulmonary fibrosis, hepatocirrhosis, nephrosclerosis, arteriosclerosis, scleroderma, myelofibrosis, chronic arthritis or rheumatoid arthritis.

7. A method according to claim 6, wherein the fibrosis is pulmonary fibrosis.

8. A method according to claim 6, wherein the fibrosis is hepatocirrhosis.

9. A method as claimed in claim 1, wherein the compound is parenterally administered at a dose of 0.5 mg to 10 mg/kg body weight per day.

10. A method as claimed in claim 1, wherein the compound is orally administered at a dose of 10 mg to 100 mg/kg body weight per day.

* * * * *